United States Patent
Lee

(10) Patent No.: US 6,542,779 B1
(45) Date of Patent: Apr. 1, 2003

(54) MAT FOR HOT-HEAT TREATMENT AND FOMENTATION

(75) Inventor: Sang-bok Lee, Taejon (KR)

(73) Assignee: Migun Medical Instrument Co., Ltd. (KR)

( * ) Notice: Subject to any disclaimer, the term of this patent is extended or adjusted under 35 U.S.C. 154(b) by 0 days.

(21) Appl. No.: 09/722,678

(22) Filed: Nov. 28, 2000

(30) Foreign Application Priority Data

Dec. 3, 1999 (KR) ............................................. 99-54663

(51) Int. Cl.⁷ .............................. A61F 2/00; A61N 1/00
(52) U.S. Cl. ......................... 607/100; 607/90; 607/154
(58) Field of Search ............................ 607/90, 91, 96, 607/98–102, 154, 156; 606/204, 237–245

(56) References Cited

U.S. PATENT DOCUMENTS

| | | | |
|---|---|---|---|
| 2,821,982 A | * | 2/1958 | Lyburn et al. |
| 4,498,462 A | * | 2/1985 | Henley |
| 4,884,574 A | * | 12/1989 | Hardie et al. |
| 5,101,809 A | * | 4/1992 | Daffer et al. |
| 5,645,578 A | * | 7/1997 | Daffer et al. ................. 607/91 |
| 5,891,186 A | * | 4/1999 | Daffer et al. ................. 607/91 |
| 6,066,087 A | * | 5/2000 | Tron ............................ 600/21 |
| 6,157,005 A | * | 12/2000 | Lu .............................. 219/400 |
| 6,243,609 B1 | * | 6/2001 | Lee ............................. 607/100 |

OTHER PUBLICATIONS

Translation of the opinion dated May 26, 2000 and translation of the decision dated Sep. 15, 2000 (Statements of Relevance) in common with Korean Registered Utility Model No. Silyong–0182020–00–00 with Cited Art Korean Publicized Utility Model No. 93–700055.

* cited by examiner

Primary Examiner—Chen-wen Jiang
(74) Attorney, Agent, or Firm—Cantor Colburn LLP

(57) ABSTRACT

A mat for hot-heat treatment and fomentation including: a compressor installed in a main body; a cool and hot wind generator for generating a cool wind or a hot wind according to a user's selection and discharging it through a discharge outlet when the compressor is operated; a cover sheet inflated with the cool wind or the hot wind generated by the cool and hot wind generator, lower end portion thereof being sealed with the marginal portion of the main body so as not to leak the cool wind or the hot wind outwardly; and a heater embedded at the bottom of the main body and heated at a predetermined temperature. With this construction, the body of the user can be heated or sweated by the cool and hot wind generator within a limited space, so that more effective hot-heat treatment can be performed.

1 Claim, 3 Drawing Sheets

HOT-HEAT TREATMENT DEVICE 100

MAT FOR HOT-HEAT TREATMENT AND FOMENTATION

BACKGROUND OF THE INVENTION

1. Field of the Invention

The present invention relates to a mat for hot-heat treatment and fomentation, and more particularly to a mat for hot-heat treatment and fomentation capable of automatically pressurizing and fomenting joints of the backbone of the body of users by a hot-heat treatment device and capable of heating and sweating the body of users by a cool and hot wind generator within a limited space, thereby providing an effective hot-heat treatment.

2. Description of the Background Art

Generally, widely used physical treatment devices for home use or installed in specific clinics largely include a hot-heat treatment device designed to pressurize and foment a diseased part of a body of a user by using a Helium lamp or an infrared lamp, and a radio frequency treatment device using a radio frequency lamp.

In case where a user desires to use the treatment device (the hot-heat treatment device or the radio frequency treatment device), the treatment device is to be accurately positioned on a spot on the body suitable for acupuncture of a joint of the backbone of the user and moved to the next joint of the backbone as certain time elapses.

However, as for this treatment, after the user puts the treatment device on the backbone by his or her hands, he or she must move it to the next backbone joint in the same manner, which, thus, is inconvenient for a patient who has a problem to move. In spite of this trouble, if the user still intends to use the treatment device, he or she would have a difficulty in accurately positioning it on the spot on the body suitable for acupuncture of the joint of the backbone, which is not satisfactorily effective for hot-heat treatment.

Therefore, recently, in an effort to overcome the shortcomings, there has been proposed a mat for hot-heat treatment which is capable of automatically pressurizing and fomenting the spots on the body suitable for acupuncture of the joints of the backbone of the user.

FIG. 1 is a plan view of a general hot-heat treatment mat. FIG. 2 is a side-sectional view of the general hot-heat treatment mat. FIG. 3 is a front view of the general hot-heat treatment mat.

As shown in the drawing, the hot-heat treatment mat includes a main body 100 in a mat type on which the user is to lie down; a reciprocal motor 200 fixed installed at a portion of the main body 100; a screw 300 idly rotated upon receipt of a driving force by a belt 210 as the reciprocal motor 200 is driven; a movable body 500 for being threaded with the screw 300 and being reciprocally moved forwardly and backward in as the screw 300 is idly rotated, the movable body having a space in a vertical direction; a treatment device moving plate 400 having a moving bar 420 at its lower surface to be inserted in the space 510 and movement rails 410 at its right and left side, on which the hot-heat treatment device is fixedly mounted; and an indented rail 600 having an indented surface 610 on which the treatment device moving plate 400 and the hot-heat treatment device are concurrently moved up and down.

In order to use the mat for hot-heat treatment, first, the hot-heat treatment device is fixedly mounted on the upper surface of the treatment device moving plate 400. And then, in a state that the user lies down on the main body 100, when electric power is applied to the reciprocal motor 200, the driving force of the reciprocal motor 200 is transferred to the screw 300 and the screw 300 is idly rotated in the direction in which the reciprocal motor 200 is driven.

Then, the movable body 500 is linearly and reciprocally moved along the screw 300. At this time, the treatment device moving plate 400 is linearly and reciprocally moved on the indented rail 600 along with the movable body 500 by the moving bar 420, and when the movement rail 410 is guided along the indented surface 610, the moving bar 420 is moved freely, so that the treatment device moving plate 400 and the hot-heat treatment device can be moved up and down, thereby pressurizing and fomenting the joints of the backbone of the user.

As described above, the general mat for hot-heat treatment is effective in the aspect that the spots on the body suitable for acupuncture of the joints of the backbone of the user can be automatically pressurized and fomented with the automatic hot-heat treatment device moved.

However, since the upper portion of the mat for hot-heat treatment is opened with no additional devices for treatment provided therein, it doesn't meet users' expectations as multi-functional products and of more effective treatment.

SUMMARY OF THE INVENTION

Therefore, an object of the present invention is to provide a mat for hot-heat treatment and fomentation including a hot-heat treatment device capable of automatically pressing and fomenting joints of the backbone of users by a hot-heat treatment device and capable of heating and sweating the body of users by a cool and hot wind generator within a limited space, thereby accomplishing a satisfactorily effective hot-heat treatment.

To achieve these and other advantages and in accordance with the purpose of the present invention, as embodied and broadly described herein, there is provided a mat for hot-heat treatment and fomentation including: a compressor installed in a main body; a cool and hot wind generator for generating a cool wind or a hot wind according to a user's selection and discharging it through a discharge outlet when the compressor is operated; a cover sheet inflated with the cool wind or the hot wind generated by the cool and hot wind generator, lower end portion thereof being sealed with the marginal portion of the main body so as not to leak the cool wind or the hot wind outwardly; and a heater embedded at the bottom of the main body and heated at a predetermined temperature.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
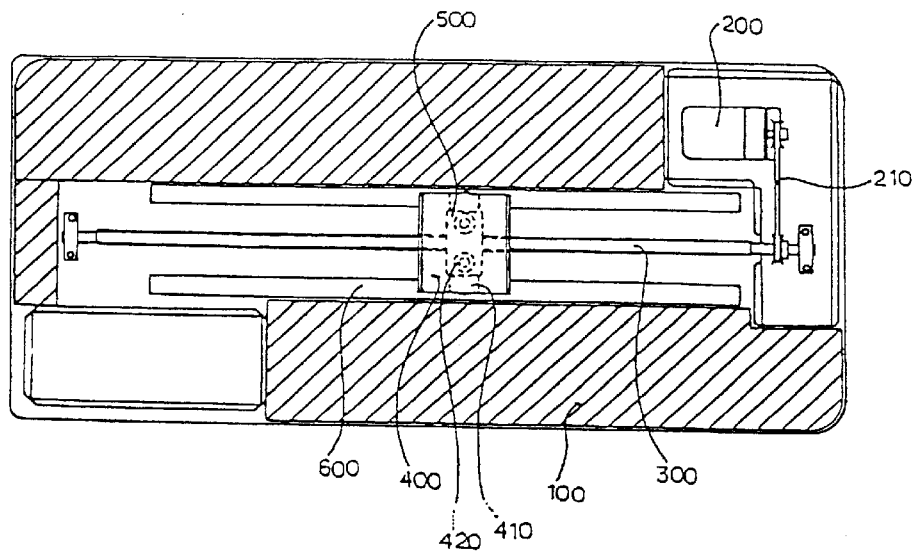
FIG. 1 is a plan view of a general mat for hot-heat treatment in accordance with a conventional art.
Figure 2:
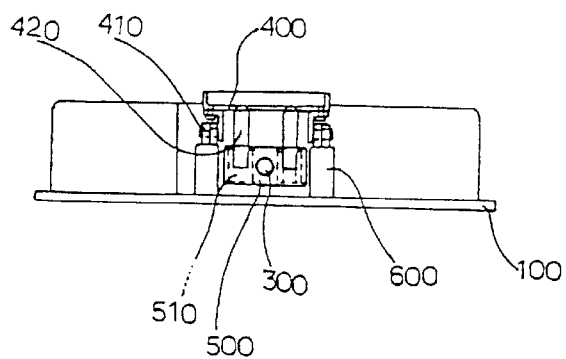
FIG. 2 is a vertical-sectional view of the general mat for hot-heat treatment in accordance with the conventional art.
Figure 3:
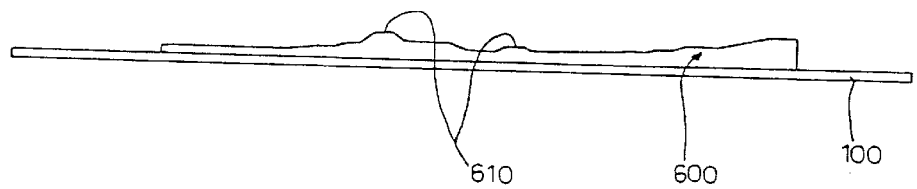
FIG. 3 is a front view of the general mat for hot-heat treatment in accordance with the conventional art.

Reference will now be made in detail to the preferred embodiments of the present invention, examples of which are illustrated in the accompanying drawings.

The mat for hot-heat treatment of the present invention has the same mat-type as that of the conventional art.

That is, the hot-heat treatment of the present invention basically includes a main body 100 in a mat type on which the user is to lie down; a reciprocal motor 200 fixed installed at a portion of the main body 100; a screw 300 idly rotated upon receipt of driving force by a belt 210 as the reciprocal motor 200 is driven; a movable body 500 for being threaded with the screw 300 and being reciprocally moved forwardly and backwardly as the screw 300 is idly rotated, the movable body having a space in a vertical direction; a treatment device moving plate 400 having a moving bar 420 at its lower portion to be inserted in the space 510 and movement rails 410 at its right and left sides, on which the hot-heat treatment device is fixedly mounted; and an indented rail 600 having an indented surface 610 on which the treatment device moving plate 400 and the hot-heat treatment device are concurrently moved upwardly and downwardly.

Figure 4:
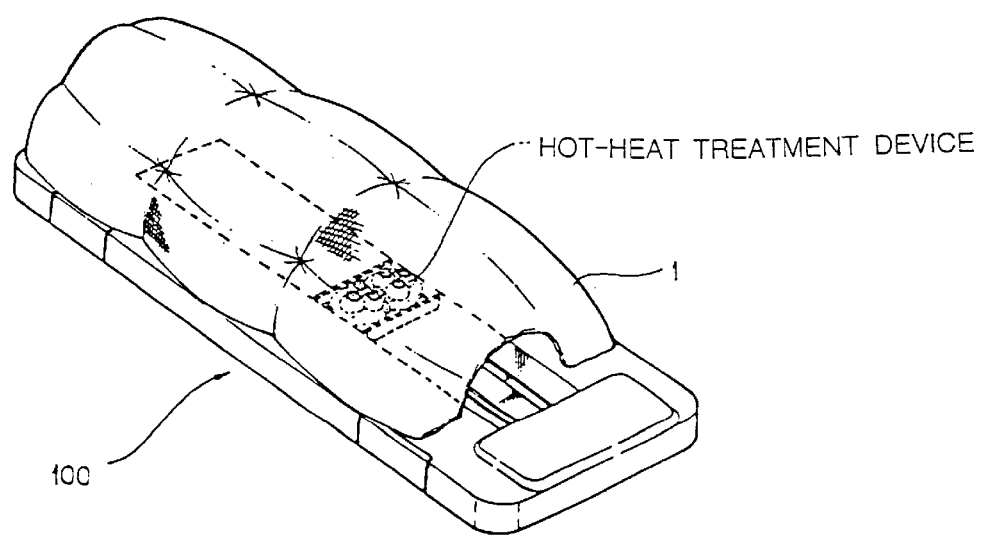
FIG. 4 is a perspective view of a mat for hot-heat treatment in accordance with the present invention.
Figure 5:
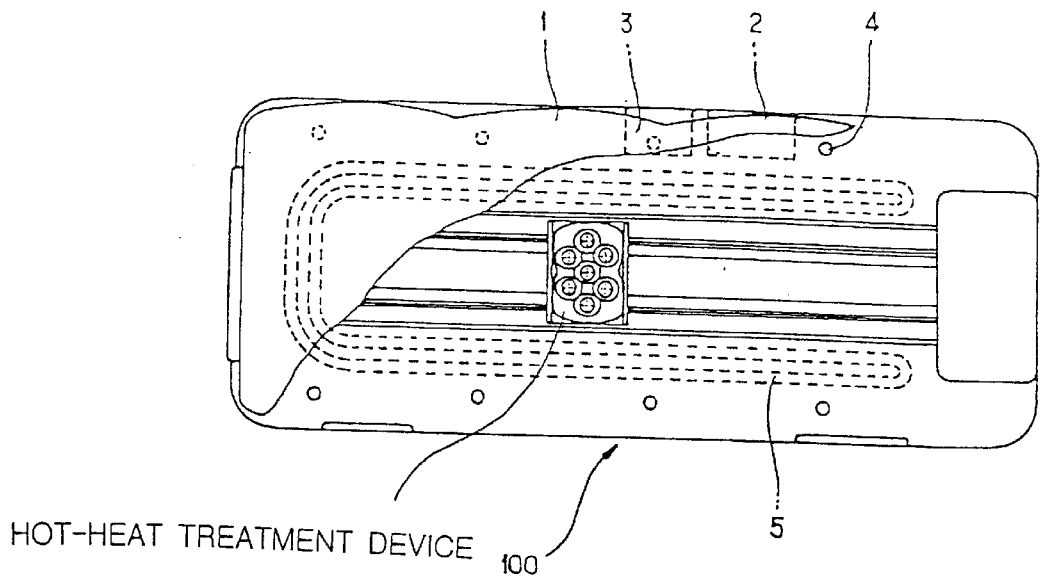
FIG. 5 is a plan view of the mat for hot-heat treatment in accordance with the present invention.
Figure 6:
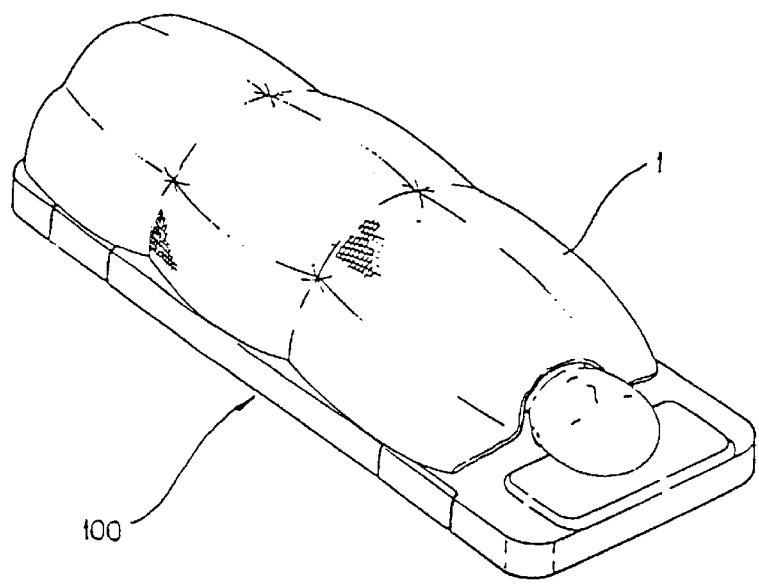
FIG. 6 is a perspective view showing a use status of the mat for hot-heat treatment in accordance with the present invention.

However, as shown in FIGS. 4 through 6, in order to have more effective treatment, the mat for hot-heat treatment of the present invention further includes a compressor 3 installed in the main body 100; a cool and hot wind generator 2 for generating a cool wind or a hot wind according to a user's selection and discharging it through a discharge outlet 4 when the compressor is operated; a cover sheet 1 inflated with the cool wind or the hot wind generated by the cool and hot wind generator 2, lower end portion thereof being sealed with the marginal portion of the main body 100 so as not to leak the cool wind or the hot wind outwardly; and a heater 5 embedded in the bottom of the main body 100 and heated at a predetermined temperature.

In this respect, the compressor 3 and the cool and hot wind generator 2 are connected in the same manner as in the typically used cool and hot wind generating structure.

The operation of the mat for hot-heat treatment of the present invention constructed as described above will now be explained.

First, the user puts his or her body in the cover sheet 1 formed at the upper portion of the main body 100, and then the main body 100 is operated. Then, the hot-heat treatment device is actuated to pressurize and foment the joints of the backbone of the user. In this respect, since the entrance of the cover sheet 1 is made of an elastic rubber band, when the user comes in, the entrance of the cover sheet 1 stretches to receive the user. After the body of the user has completely come in the mat with his or her head exposed outside, the entrance of the cover sheet 1 is contracted to its original form and maintained as it is.

In this state, the cool and hot wind generator 2 is actuated by the compressor 3 to generate a cool wind or a hot wind according to the user's selection. The cool wind or the hot wind is discharged into the main body 100 through the discharging outlet 4, inflating the cover sheet 1, without being exhausted outwardly, thereby performing cool fomenting or hot fomenting with the user. And, at this time, the heater 5 raises the temperature of the whole bottom surface of the main body 100 to a predetermined level.

As so far described, according to the mat for hot-heat treatment of the present invention, since the cover sheet is provided with the main body, in which the hot-heat treatment device is automatically moved and the cool and hot wind generator is integrally formed to generate the cool wind or the hot wind, the joints of the backbone of the user can be automatically pressurized and fomented by the hot-heat treatment device, which is like in the conventional art. Furthermore, in the present invention, since the body of the user can be heated or sweated by the cool and hot wind generator in a limited space, more effective hot-heat treatment can be performed.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalence of such meets and bounds are therefore intended to be embraced by the appended claims.

What is claimed is:

1. A mat for hot heat treatment, comprising:

a main body on which a user lies down;

a reciprocal motor disposed at a portion of the main body;

a screw rotatable upon receipt of a driving force by a belt as the reciprocal motor is driven;

a movable body threaded with the screw and being movable forwardly and backwardly as the screw is rotated, the movable body having a space in a vertical direction;

a treatment device moving plate having a moving bar at a lower portion to be inserted in the space and movement rails at right and left sides, on which a hot-heat treatment device is disposed;

an indented rail having an indented surface on which the treatment device moving plate and the hot-heat treatment device are concurrently moved upwardly and downwardly;

a compressor installed in the main body;

a cool and hot wind generator for generating a cool wind or a hot wind according to the user's selection and discharging the cool wind or the hot wind through a discharge outlet when the compressor is operated;

a cover sheet inflated with the cool wind or the hot wind, a lower end portion thereof being sealed with a marginal portion of the main body so as not to leak the cool wind or the hot wind outwardly; and a heater embedded at a bottom of the main body and heated at a predetermined temperature.

* * * * *